United States Patent [19]

Burrington et al.

[11] Patent Number: 4,473,506

[45] Date of Patent: Sep. 25, 1984

[54] IRON SELENIUM TELLURIUM OXIDE CATALYSTS

[75] Inventors: James D. Burrington, Richmond Hts.; James F. Brazdil, Lyndhurst; Robert K. Grasselli, Chagrin Falls, all of Ohio

[73] Assignee: The Standard Oil Company, Cleveland, Ohio

[21] Appl. No.: 434,794

[22] Filed: Oct. 18, 1982

[51] Int. Cl.$^3$ .................. C07C 120/14; C07C 51/21; C07C 5/32

[52] U.S. Cl. .................. 260/465.3; 260/465.9; 562/546; 568/477; 568/479; 568/480; 568/481; 585/627; 585/629; 585/630; 502/215

[58] Field of Search .................... 260/465.3

[56] References Cited

U.S. PATENT DOCUMENTS

| | | | |
|---|---|---|---|
| 2,383,711 | 8/1945 | Clark et al. | 260/597 |
| 3,232,978 | 2/1966 | Yasahara et al. | 260/465.3 |
| 3,335,169 | 8/1967 | Eden | 260/465.3 |
| 3,392,187 | 7/1968 | Eden | 260/465.3 |
| 3,392,188 | 7/1968 | Eden | 260/465.3 |
| 3,392,189 | 7/1968 | Eden | 260/465.3 |
| 3,396,189 | 8/1968 | Eden | 260/465.3 |
| 3,412,135 | 11/1968 | Eden | 260/465.3 |
| 3,417,125 | 12/1968 | Eden | 260/465.3 |
| 3,417,128 | 12/1968 | Eden | 260/465.3 |
| 3,426,059 | 2/1969 | Eden | 260/465.3 |
| 3,426,060 | 2/1969 | Eden | 260/465.3 |
| 3,641,102 | 2/1972 | Reuiet et al. | 260/465.3 |
| 3,784,560 | 1/1974 | Yoshino et al. | 260/465.3 |
| 3,803,207 | 4/1974 | Tellier et al. | 260/465.3 |
| 3,900,426 | 8/1975 | Fattore et al. | 260/465.3 X |
| 3,969,390 | 7/1976 | Faletti et al. | 260/465.3 |
| 3,988,359 | 10/1976 | Saito et al. | 260/465.3 |
| 4,219,670 | 8/1980 | Okada et al. | 562/546 |

OTHER PUBLICATIONS

Derwent Abstract of Japan 78260 D/43 (1979).
Derwent Abstract of Japan 48359 D/27 (1980).

*Primary Examiner*—Joseph Paul Brust
*Attorney, Agent, or Firm*—Charles S. Lynch; John E. Miller, Jr.; Larry W. Evans

[57] ABSTRACT

Oxide complex catalysts of iron, selenium and tellurium provide good yields of acrylonitrile in the ammoxidation of propylene with high selectivities at low temperature.

11 Claims, No Drawings

IRON SELENIUM TELLURIUM OXIDE CATALYSTS

BACKGROUND OF THE INVENTION

The present invention relates to new catalyst systems for ammoxidizing propylene to produce acrylonitrile and for carrying out other oxidation-type reactions such as the oxidation of unsaturated olefins to produce the corresponding aldehydes and acids and the oxydehydrogenation of various olefins to produce diolefins.

Catalytic ammoxidation of propylene to produce acrylonitrile is a well known process. Many different catalysts have been described in the literature as effective in this process. Normally, it is indicated that such catalysts are effective at temperatures between about 200° and 600° C. The reaction, however, is very temperature sensitive and as a practical matter, temperatures on the order of 380° to 400° C. are necessary to produce significant amounts of acrylonitrile.

Most ammoxidation catalysts are formulated so as to maximize the yields of acrylonitrile, i.e. the amount of acrylonitrile produced based on the amount of propylene fed. The ammoxidation of propylene is normally carried out in a single pass mode, i.e. without recycle, and consequently maximizing single pass yields produces the greatest amount of acrylonitrile based on the amount of reactant used. However, it is possible to carry out the ammoxidation reaction in a recycle mode wherein some or all of the gross reaction product or unreacted reactants are recycled. In this situation, catalysts having superior selectivities, i.e. the ability to catalyze the reaction of interest as opposed to undesired side reactions, are more attractive. Unfortunately, catalysts which are formulated so as to produce acrylonitrile in high yields exhibit less that optimum selectivities.

Accordingly, it is an object of the present invention to provide a new class of catalysts suited for use in the ammoxidation of propylene and its homolog isobutylene to acrylonitrile or methacrylonitrile which exhibits high selectivities to the desired product and are also capable of operating at lower temperatures than conventional.

SUMMARY OF THE INVENTION

These and other objects are accomplished by the present invention which is based on the discovery that oxide complex catalysts of iron, selenium and tellurium exhibit excellent catalytic properties for the ammoxidation of propylene to acrylonitrile at high acrylonitrile selectivities and at comparatively low temperatures.

Thus, the present invention provides a novel process for ammoxidizing propylene to produce acrylonitrile by contacting propylene, ammonia and molecular oxygen with an oxide complex catalyst at elevated temperature, the improvement comprising employing as the catalyst an oxide complex of the following formula:

$$A_aD_bE_cFe_dSe_eTe_fO_x$$

wherein
A is a Group IA element, a Group IIA element, Tl, Sm or mixtures thereof;
D is Mo, W, Sb, P, B, S, Pb, Zn, a Rare Earth element or mixtures thereof;
E is Cu, Cr, V, Y, Al, U, Co, Mn, Ru, Sn, As or mixtures thereof; and
a is 0 to 10;
b is 0 to 10;
c is 0 to 10;
d is 0 to 20;
e is 0 to 20;
f is 0 to 20, with the proviso that only one of d, e and f can be zero in any particular catalyst,

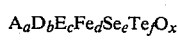

is less than 1.
b is less than e+f when D is Mo and/or W.

are each less than 0.8, and
x is a number sufficient to satisfy the valence requirements of the other elements present, the W/(Se+Te) ratio in said catalysts being less than 0.05.

It has also been found that the catalysts employed in the above reaction are useful in other related reactions such as the oxidation of olefins, aldehydes and alcohols to aldehydes and acids and the oxydehydrogenation of olefins to diolefins. Accordingly, the present invention further provides processes for the oxydehydrogenation of olefins to diolefins and the oxidation of olefins to aldehydes and acids and the oxidation of alcohols to various oxidation products, the improvement in accordance with the present invention comprising using as the catalyst an oxide complex as described above.

DETAILED DESCRIPTION

Catalysts

The catalysts employed in the present invention are oxide complex redox catalysts. In other words, the catalysts are composed of a number of different oxides arranged in some complex form, the exact nature of which is not understood. They function by a redox mechanism, i.e. in use the catalysts continuously gain and loose oxygen. Redox catalysts are well known and have been used for many years in the above reactions.

The catalysts employed in the present invention are oxide complexes of the following general formula:

$$A_aD_bE_cFe_dSe_eTe_fO_x$$

wherein
A is a Group IA element, a Group IIA element, Tl, Sm or mixtures thereof, preferably K, Rb and/or Cs;
D is Mo, Sb, P, B, S, Pb, Zn, a Rare Earth element or mixtures thereof;
E is Cu, Cr, V, Y, Al, U, Co, Mn, Ru, Sn, As or mixtures thereof; and
a is 0 to 10;
b is 0 to 10;
c is 0 to 10, preferably 0.1 to 20;
d is 0 to 20, preferably 0.1 to 20;
e is 0 to 20, preferably 0.1 to 20;
f is 0 to 20, preferably 0.1 to 20, with the proviso that only one of d, e and f can be zero in any particular catalyst $$\frac{a+b+c}{d+e+f}$$

is less than 1, preferably less than 0.5, more preferably less than 0.3, b is less than e+f when D is Mo and/or W, $$\frac{d}{d+e+f}, \frac{e}{d+e+f} \text{ and } \frac{f}{d+e+f}$$

are each less than 0.8, preferably less than 0.6, and x is a number sufficient to satisfy the valence requirements of the other elements present, the W/(Se+Te) ratio in said catalysts being less than 0.05.

When the catalysts of the invention contain molybdenum, the molybdenum content is less than the sum of the selenium and tellurium contents (i.e. b<e+f). In addition, when the catalysts of the invention contain vanadium, the vanadium content is less than one half the sum of the tellurium and selenium contents and also less than one half the iron content. Also, when the catalyst of the invention contain antimony, they must also contain selenium. Preferably, the catalysts are free of vanadium and antimony and tungsten.

When the catalysts of the invention are used in the oxidation of olefins to produce aldehydes and acids or in the oxydehydrogenation of olefins to produce diolefins, they may further contain tungsten (i.e. D can also be W) provided they also contain selenium.

Especially preferred catalysts are those containing iron, selenium and tellurium in which during preparation the tellurium is added to the other components of the catalyst in a valence state of greater than 4, preferably greater than 5. In this connection, tellurium can be added to the other components of the catalyst during preparation in a variety of different forms, e.g. as telluric acid or as tellurium dioxide. Tellurium dioxide is preferred since it is is least expensive. In accordance with the preferred embodiment of the invention, however, it has been found that the tellurium should be in a valence state greater than 4. When telluric acid is used as the tellurium source, it can be added to the other components as is since the tellurium in telluric acid has a valence state of +6. However, since the tellurium in tellurium dioxide has a valence state of +4, it is preferable in accordance with this aspect of the invention to subject the tellurium dioxide to oxidation before adding it to the remaining components. This can be easily accomplished, for example, by digesting the tellurium dioxide with an oxidant such as hydrogen peroxide or nitric acid.

The catalysts of the invention can be used either in unsupported form or supported on suitable carriers such as $SiO_2$, $Al_2O_3$, $BPO_4$, $SbPO_4$, $ZrO_2$, $TiO_2$, Alundum and the like. The catalysts can also be coated on these supports by special techniques known in the art.

These catalysts can be prepared by conventional techniques such as disclosed in Grasselli, et al, U.S. Pat. No. 3,642,930. These catalysts are most easily prepared by slurry techniques wherein an aqueous slurry containing all of the elements in the objective catalyst is produced, the water removed from the aqueous slurry to form a precatalyst precipitate gel or powder and the precatalyst then heated in the presence of an oxygen-containing gas such as air at elevated temperature to calcine the precatalyst thereby forming the catalyst.

Liquids other than water, such as $C_1$ to $C_8$ alcohols can also be used to form the precatalyst slurry.

Ammoxidation

The catalysts of the invention find significant use in the ammoxidation of propylene to produce acrylonitrile. This reaction is well known and described, for example, in the above-noted Grasselli, et al. patent. In general, the ammoxidation reaction is accomplished by contacting the reactant, oxygen and ammonia with a particular catalyst in the vapor phase. The inventive reaction is carried out in the same manner and under the conditions generally set forth in this patent except for temperature as discussed below.

In this connection, while the prior art in this area in general indicates that the ammoxidation process can be carried out at temperatures between about 200° and 600° C., experience has shown that temperatures on the order of at least about 400° C. are necessary to produce significant amounts of acrylonitrile. In accordance with the present invention the catalysts, although generally effective between 200° to 600° C., show significant effectiveness at much lower temperatures than prior art catalysts, e.g. about 250° to 380° C., preferably 300° to 350° C.

In a preferred aspect, the inventive process comprises contacting a mixture comprising propylene, ammonia and oxygen with the catalyst of this invention at an elevated temperature and at atmospheric or near atmospheric pressure.

Any source of oxygen may be employed in this process. For economic reasons, however, it is preferred that air be employed as the source of oxygen. From a purely technical viewopoint, relatively pure molecular oxygen will give similar results. The molar ratio of oxygen to the olefin in the feed to the reaction vessel should be in the range of 0.2:1 to 20:1, preferably 0.5:1 to 4:1, more preferably 1:1 to 3:1.

Low molecular weight saturated hydrocarbons do not appear to influence the reaction to an appreciable degree, and these materials can be present; consequently, the addition of saturated hydrocarbons to the reaction feed is contemplated within the scope of this invention. Likewise, diluents, such as nitrogen and oxides of carbon may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obrained at ammonia-olefin ratios substantially below 1:1, i.e. in the range of 0.15:1 to 0.75:1. Above the upper limit of this range, the amount of aldehydes produced rapidly decreases. Within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are within the scope of the present invention and are preferred in the fluid-bed operation.

In general, the molar ratio of added water to olefin, when water is added, is in the neighborhood of 0.1:1 or higher. Ratios on the order of 1:1 to 6:1 are particularly desirable, but higher ratios may be employed, i.e. up to about 10:1.

The reaction should be carried out at about atmospheric or slightly above atmospheric (2 to 3 atmospheres) pressure. In general, high pressrue, i.e. about 15 atmospheres, are not suitable since higher pressures tend to favor the formation of undesireable by-products.

The apparent contact time is not critical, and contact times in the range of from 0.1 to 40 seconds may be employed. The optimal contact time will, of course, vary depending upon the reactant being used, but in general, contact time of from 1 to 15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a vapor. Conventionally, this gaseous reaction product is treated to remove $NH_3$ and then partially condensed either by indirect contact with a cooling medium or direct contact with water to form a liquid phase containing acrlyonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

In addition to propylene, other hydrocarbons and oxgenated hydrocarbons can be ammoxidized with the catalysts of the invention. For example, alcohols such as isopropanol, n-propanol, t-butanol, and aldehydes such as acrolein and methacrolein can be readily converted to nitriles in accordance with the present invention. In addition to propylene, other preferred starting materials are aldehydes and alcohols containing three or four carbon atoms. The general ammoxidation process for converting olefins, alcohols and aldehydes to nitrile is well known and described for example is U.S. Pat. No. 3,456,138, the disclosure of which is incorporated herein by reference.

Oxidation

The catalysts of this invention can also be employed in the catalyst oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain). Instead of olefins, alcohols such as isopropanol, n-propanol or t-butanol can be used as reactants.

The olefins or alcohols may be in admixture with paraffinic hydrocarbons, such as ethane, propane, butane and pentane. For example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° to 600° C. may be advantageously employed. However, the process may be conducted at other pressures, and in the case where superatmospheric pressures, e.g. about 5 atmospheres are employed, somewhat lower temperatures are possible. In the case where this process is employed to convert propylene to acrolein, a temperature range of 200° to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired by-products and waste is diminished.

The apparent contact time employed in the process is not critical and it may be selected from a broad operable range which may vary from 0.1 to 50 seconds. The apparent contact times may be defined as the length of time in seconds which a unit volume of gas measured under the conditions of reaction is in contact with the apparent unit volume of the catalyst. It may be calculated, for example, from the apparent volume of the catalyst be, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:0.25 to 1:10 will give very satisfactory results while a ratio of 1:0.5 to 1:6 has been found the optimum when converting propylene to acrolein.

Inert diluents such as nitrogen and carbon dioxide may be present in the reaction mixture.

Oxydehydrogenation

In accordance with the present invention, the catalyst system of the present invention can also be employed in the catalytic oxidative dehydrogenation of olefins to diolefins and aromatic compounds. In this process, the feed stream in vapor from containing the olefin to be dehydrogenation and oxygen is conducted over the catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquanternary carbon atoms, of which at least four are arranged in series in a straight chain or ring. The olefins preferably are either normal straight chains or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methylbutene-1, 2-methylbutene-2,4-methylpentene-2; heptene-1; 3,4-dimethylpentene-1; octene-1; cyclopentene; cyclohexene, 3-methyl cyclohexene and cycloheptene.

Open chain olefins yield diolefins and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within range of from about 200° to 800° C. Optimum yields are obtainable at temperatures within the range from about 300° to 600° C.

The preferred reaction pressure is approximately atmospheric, within the range of from about 0.1 to about 5 atmospheres.

Only a brief contact time with the catalyst is required for effective oxydehydrogenation. The apparent contact time with the catalyst can vary from about 0.1 up to about 50 seconds but higher contact times can be used if desired. At the short contact times, comparatively small reactors and small amounts of catalyst can be used effectively.

Process Conditions

In carrying out the foregoing processes, any apparatus of the type suitable for carrying out the oxidation reactions in the vapor phase may be employed. The processes may be conducted either continuously or intermittently. The catalyst may be a fixed-bed employing a particulate or pelleted catalyst or, in the alternative, a fluid-bed catalyst may be employed which is normally micro-spheroidal.

WORKING EXAMPLES

In order to more thoroughly describe the present invention, the following working examples are presented. In these examples, the following definitions apply:

"Conversion" means $$\frac{\text{moles reactant reacted}}{\text{moles reactant fed}} \times 100$$

"Selectivity" means $$\frac{\text{moles product formed}}{\text{moles reactant reacted}} \times 100$$

In each of the examples and comparative example, a catalyst having the composition set forth in the following tables was prepared in accordance with a standard laboratory preparation. For example, the catalyst of Example 4 was prepared as follows:

23.94 gm tellurium dioxide was added to about 20 ml of 30 percent aqueous $H_2O_2$ with stirring. The mixture was heated to about 80° C. and held there for 2½ hours. 16.64 gm $SeO_2$ was dissolved in 50 ml distilled $H_2O$ and added to the tellurium dioxide mixture. 36.67 gm silica was then added to the resultant composition.

In a separate beaker, 60.60 gm $Fe(NO_3)_3 \cdot 9H_2O + 1.52$ gm $KNO_3$ were dissolved in about 100 ml distilled water. This solution was then added with stirring to the previously prepared selenium-tellurium-silica mixture. The pH of the resultant slurry was adjusted to about 3 by the drop-wise addition of concentrated ammonium hydroxide. The slurry was then heated and stirred to remove excess water and then dried at 120° C. for about 16 hours.

The dry material was then heated for about 3 hours at 290° C., ground and then calcined at 380° C. for 3 hours.

EXAMPLES 1 TO 7

A number of catalysts in accordance with the invention were tested in the known ammoxidation reaction for producing acrylonitrile from propylene. In each example and comparative example, 1.5 cc of catalyst were charged into a 6 cc reactor and contacted with a feed comprising 1.0 propylene/1.2 $NH_3$/10.5 air/4 $H_2O$ at a reaction temperature of 320° C. and a contact time of 3 seconds. The gross reaction product recovered from each experiment was then analyzed.

The composition of the catalysts and the results obtained are set forth in the following Table 1. Unless otherwise indicated, all catalysts were supported on 20 wt. silica. Also, the catalysts of Examples 1 to 3 were produced by a procedure using tellurium dioxide as is as a source for tellurium. In Examples 4 to 7, however, the tellurium dioxide was digested in hydrogen peroxide to yield tellurium in an average valence state greater than 4 before being added to the other components of the catalyst.

TABLE 1

AMMOXIDATION OF PROPYLENE

Feed: 1 propylene/1.2 $NH_3$/10.5 Air/4 $H_2O$
Reaction Temperature: 320° C. Contact Time = 3 seconds
All catalysts are supported on 20 $SiO_2$

| Ex. No. | Catalyst | Propylene Conversion | Selectivity | |
|---|---|---|---|---|
| | | | Acrylonitrile | Acrylonitrile plus HCN |
| 1 | $FeTeO_x$ | 1.4 | 72.2 | — |
| 2 | $FeSeO_x$ | 26.4 | 73.5 | 80.4 |
| 3 | $FeSeTeO_x$ | 25.1 | 70.5 | 73.1 |
| 4 | $FeSeTeO_x$ | 52.7 | 85.2 | 86.0 |
| 5 | $K_{0.1}FeSeTeO_x$ | 33.5 | 88.3 | 89.0 |
| 6 | $Cs_{0.05}FeSeTeO_x$ | 45.0 | 88.2 | 88.8 |
| 7 | $FeTeO_x$ | 15.1 | 88.7 | 93.0 |

From the above, it can be seen that the catalysts of the invention are capable of ammoxidizing propylene to acrylonitrile at the comparatively low temperature of 320° C. with high selectivities to acrylonitrile and high selectivities to acrylonitrile plus HCN, another valuable product of the reaction. In addition, comparison of Examples 2 and 3 with Example 1 and comparison of Example 7 with Example 4 shows that selenium is an important component in terms of the activity (i.e. conversion) on the catalysts. Further, comparison of Examples 4 to 7 with Examples 1 to 3 shows the importance to both activity (i.e. conversion) and selectivity of supplying tellurium to the catalyst during preparation in a valence state greater than 4.

EXAMPLES 8 TO 20

Examples 1 to 7 were repeated using a number of different catalysts in accordance with the present invention. In addition, the reaction temperature and the contact times wer varied. Also, the feed was changed to 1 propylene/1.2 NH$_3$/4.0 H$_2$O/55 air. The results obtained are set forth in the following Table 2:

TABLE 2
AMMOXIDATION OF PROPYLENE

Feed: 1 propylene/1.2 NH$_3$/4.0 H$_2$O/55 air
All catalysts are supported on 20 wt. % SiO$_2$

| EX. NO. | CATALYST | TEMP.° C. | CONTACT TIME | PROPYLENE CONVERSION | SELECTIVITY ACRYLONITRILE | ACRYLONITRILE + HCN |
|---|---|---|---|---|---|---|
| 8 | SeFe$_{0.98}$O$_x$ | 260 | 4.0 | 14.4 | 59.0 | 77.0 |
| 9 | SeFe$_{0.81}$O$_x$ | 320 | 1.0 | 8.0 | 82.8 | 89.7 |
| 10 | SeFe$_{0.81}$O$_x$ | 370 | 2.8 | 75.4 | 42.2 | 43.0 |
| 11 | Se$_{0.7}$Fe$_{1.0}$Mo$_{0.9}$O$_x$ | 270 | 0.5 | 5.6 | 14.2 | 39.3 |
| 12 | Se$_{0.7}$Fe$_{1.0}$Mo$_{0.9}$O$_x$ | 285 | 0.26 | 100.0 | 27.1 | 33.9 |
| 13 | Se$_{0.7}$Fe$_{1.0}$Mo$_{0.9}$O$_x$ | 300 | 0.5 | 100.0 | 32.6 | 34.6 |
| 14 | Se$_{1.0}$Fe$_{3.2}$Mo$_{3.1}$O$_x$ | 320 | 1.0 | 58.4 | 54.2 | 70.5 |
| 15 | Se$_{1.0}$Fe$_{1.0}$Te$_{0.6}$O$_x$ | 250 | 0.9 | 18.2 | 61.5 | 80.7 |
| 16 | Se$_{1.0}$Fe$_{0.83}$Te$_{0.68}$O$_x$ | 320 | 1.0 | 35.0 | 95.9 | 98.4 |
| 17 | Se$_{1.0}$Fe$_{0.83}$Te$_{0.68}$O$_x$ | 320 | 6.0 | 100.0 | 86.9 | 90.0 |
| 18 | Se$_{1.0}$Fe$_{0.83}$Te$_{0.68}$O$_x$ | 350 | 1.0 | 37.7 | 88.3 | 91.9 |
| 19 | Se$_{1.0}$Fe$_{0.83}$Te$_{0.68}$O$_x$ | 350 | 5.9 | 100.0 | 58.0 | 60.0 |
| 20 | Se$_{1.0}$Fe$_{0.83}$Te$_{0.68}$O$_x$ | 380 | 0.9 | 64.9 | 15.8 | 17.1 |

The above examples further show that the catalysts of the invention are capable of ammoxidizing propylene at various temperatures below 380° C. and at various contact times.

Although only a few embodiments of the invention have been described above, it should be appreciated that many modifications can be made without departing from the spirit and scope of the invention. All such modifications are intended to be included within the scope of the present invention, which is to be limited only by the following claims:

We claim:

1. In a process for the ammoxidation of propylene or isobutylene by contacting propylene or isobutylene with ammonia and molecular oxygen at a temperature of 200° to 600° C. to produce acrylonitrile or methacrylonitrile, the improvement comprising employing as said catalyst an oxide complex redox catalyst of the formula:

$$A_aD_bE_cFe_dSe_eTe_fO_x$$

wherein
A is a Group IA element, a Group IIA element, Tl, Sm or mixtures thereof;
D is Mo, W, Sb, P, B, S, Pb, Zn, a Rare Earth element or mixtures thereof;
E is Cu, Cr, Ce, V, Y, Al, U, Co, Mn, Ru, Sn, As or mixtures thereof; and
a is 0 to 10;
b is 0 to 10;
c is 0 to 10;
d is 0.1 to 20;
e is 0.1 to 20;
f is 0.1 to 20, $$\frac{a+b+c}{d+e+f}$$

is less than 1,
b is less than e+f when D is Mo, $$\frac{d}{d+e+f}, \frac{e}{d+e+f} \text{ and } \frac{f}{d+e+f}$$

are each less than 0.8, and
x is a number sufficient to satisfy the valence requirements of the other elements present, the W/(Se+Te) ratio in said catalysts being less than 0.05, the vanadium content in said catalysts, if any, being less than one-half the sum of the selenium and tellurium contents and less than one-half the iron content, the molybdenum content in said catalysts, if selenium contents, said catalysts containing selenium when all or part of D is Sb.

2. The process of claim 1 wherein $$\frac{a+b+c}{d+e+f}$$

is less than 1.

3. The process of claim 2 wherein $$\frac{a+b+c}{d+e+f}$$

is less than 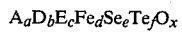.

4. The process of claim 2 wherein the content of Mo, and V, if any, are each individually less than the sum of the tellurium and selenium contents.

5. The process of claim 4 wherein the vanadium content in said catalyst, if any, is less than the sum of the tellurium and selenium contents.

6. The process of claim 5 wherein tellurium when combined with the other elements of said catalyst during the preparation thereof has an average valence state of above 4.

7. The process of claim 6 wherein tellurium when combined with the other elements of said catalyst during preparation has an average valence state of above 5.

8. The process of claim 1 wherein tellurium when combined with the other elements of said catalyst during the preparation thereof has an average valence state of above 4.

9. The process of claim 8 wherein tellurium when combined with the other elements of said catalyst during preparation has an average valence state of above 5.

10. The process of claim 1 wherein said catalyst is free of tungsten, vanadium and antimony.

11. The process of claim 1 wherein said catalyst contains tungsten.

* * * * *